(12) United States Patent
Rosa et al.

(10) Patent No.: US 9,144,456 B2
(45) Date of Patent: Sep. 29, 2015

(54) SURGICAL INSTRUMENT CONTROL

(71) Applicant: INTUITIVE SURGICAL OPERATIONS, INC., Sunnyvale, CA (US)

(72) Inventors: David J. Rosa, San Jose, CA (US); Salvatore J. Brogna, Pleasanton, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 280 days.

(21) Appl. No.: 13/834,760

(22) Filed: Mar. 15, 2013

(65) Prior Publication Data
US 2013/0267950 A1    Oct. 10, 2013

Related U.S. Application Data

(60) Provisional application No. 61/621,974, filed on Apr. 9, 2012.

(51) Int. Cl.
| A61B 18/18 | (2006.01) |
|---|---|
| A61B 18/14 | (2006.01) |
| A61B 18/12 | (2006.01) |
| A61B 17/00 | (2006.01) |
| A61B 18/00 | (2006.01) |

(52) U.S. Cl.
CPC ......... *A61B 18/1445* (2013.01); *A61B 18/1206* (2013.01); *A61B 18/1447* (2013.01); *A61B 2017/00973* (2013.01); *A61B 2018/0063* (2013.01); *A61B 2018/00601* (2013.01)

(58) Field of Classification Search
CPC ........... A61B 18/1206; A61B 18/1445; A61B 2017/00973; A61B 2018/00601; A61B 2018/0063; A61B 18/1447
See application file for complete search history.

(56) References Cited

U.S. PATENT DOCUMENTS

| 6,905,497 B2 | 6/2005 | Truckai et al. |
|---|---|---|
| 7,303,107 B2 | 12/2007 | Milliman et al. |
| 7,784,662 B2 | 8/2010 | Wales et al. |
| 7,861,906 B2 | 1/2011 | Doll et al. |
| 8,161,977 B2 * | 4/2012 | Shelton et al. ................ 128/898 |
| 2003/0114851 A1 | 6/2003 | Truckai et al. |
| 2009/0076534 A1 | 3/2009 | Shelton, IV et al. |
| 2010/0228250 A1 | 9/2010 | Brogna |
| 2011/0155781 A1 | 6/2011 | Swensgard et al. |
| 2011/0240714 A1 | 10/2011 | Whitman et al. |
| 2011/0297729 A1 | 12/2011 | Whitman et al. |
| 2012/0205419 A1 | 8/2012 | Weir et al. |
| 2012/0209288 A1 | 8/2012 | Robinson |
| 2012/0209314 A1 | 8/2012 | Weir et al. |
| 2012/0215220 A1 | 8/2012 | Manzo et al. |
| 2012/0248167 A1 | 10/2012 | Flanagan et al. |
| 2013/0103050 A1 | 4/2013 | Richmond et al. |

OTHER PUBLICATIONS

International Search Report and Written Opinion for Application No. PCT/US2013/035479, mailed on Jul. 11, 2013, 11 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

*Primary Examiner* — George Manuel

(57) ABSTRACT

In a surgical instrument, a reciprocating element controls jaw opening and closing as it moves over a first range of motion and cuts tissue clamped between the jaws as it moves over a second range of motion. A first control input controls the reciprocating element's motion over the first range of motion, and a second control input controls the reciprocating element's motion over the second range of motion. As a result, over control by the first control input will not result in inadvertent tissue cutting.

24 Claims, 6 Drawing Sheets

SURGICAL INSTRUMENT CONTROL

CROSS-REFERENCE TO RELATED APPLICATIONS

This application claims priority to U.S. Provisional Patent Application No. 61/621,974, filed on Apr. 9, 2012, which is incorporated herein by reference in its entirety.

TECHNICAL FIELD

Aspects of the present disclosure concern surgical instrument control, and more particularly concern safe control of a surgical instrument cutting function.

INTRODUCTION

Certain hand-operated surgical tools use an I-beam shaped component to slide over and compress jaws together in order to provide a uniform compressive force on tissue to be fused. As the component slides over the jaws, the component's leading edge cuts tissue held between the jaws. An example of such a tool is a rounded tip Enseal® tissue sealer using I-Blade® technology, as commercialized by Ethicon Endo-Surgery, Inc.

Since the same moving component is used to close the jaws, compress the tissue between the jaws, and cut the compressed tissue, it is possible to inadvertently cut tissue while closing the jaws in a simple tissue grasping operation, or to cut tissue ahead of a complete tissue fusing. To prevent such inadvertent cutting, a movable mechanical stop is used to prevent the component from moving beyond its jaw closure function and into its cutting function. If an operator fails to properly set the mechanical stop, however, tissue grasped between the jaws may be partially cut, either with or without the application of electrosurgical tissue fusing energy. The result is that a patient is needlessly injured (e.g., tissue is inadvertently cut during grasping; tissue intended to be fused is cut before fusing is complete, with resulting bleeding; etc.). In addition, during minimally invasive surgery, controlling bleeding that may result from such an inadvertent cutting or incomplete fusing may be difficult and time consuming, exposing the patient to further risk. What is needed, therefore, is a way to take advantage of the benefits of the jaw closure, clamping, and cutting mechanism while preventing the risk of inadvertent cutting.

SUMMARY

The present teachings may solve one or more of the above-mentioned problems and/or may demonstrate one or more of the above-mentioned desirable features. Other features and/or advantages may become apparent from the description that follows.

In accordance with various exemplary embodiments, the present teachings contemplate a computer-controlled surgical system that comprises a surgical instrument having a working end and a control system configured to separately control a grasping function of the working end and a cutting function of the working end. The control system can be operatively connected to a first input device for controlling the grasping function of the working end and can be operatively connected to a second input device for controlling the cutting function of the working end.

In accordance with various exemplary embodiments, the present teachings contemplate a method of controlling multiple functions of a working end of a computer-controlled surgical instrument. The method comprises controlling a clamping function of the working end of the instrument in response to input received from a first input device. The method further comprises separately controlling a cutting function of the working end of the instrument in response to input received from a second input device.

Additional objects and advantages of the present teachings will be set forth in part in the description which follows, and in part will be obvious from the description, or may be learned by practice of the present disclosure and/or claims. At least some of those objects and advantages of the present disclosure will be realized and attained by means of the elements and combinations particularly pointed out in the appended claims.

It is to be understood that both the foregoing general description and the following detailed description are exemplary and explanatory only and are not restrictive of the present disclosure and claims, which are entitled to their full breadth of scope including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

This description and the accompanying drawings that illustrate exemplary embodiments should not be taken as limiting, with the claims defining the scope of the present disclosure. Various mechanical, compositional, structural, electrical, and operational changes may be made without departing from the scope of this description and the present teachings as claimed, including equivalents. In some instances, well-known structures, and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained by the present teachings. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

In accordance with various exemplary embodiments, the present disclosure contemplates a surgical instrument, such as an electrosurgical instrument, that includes a shaft and a working end (end effector). The working end of the instrument includes components operable to perform gripping, cutting, and fusing procedures. The surgical instrument may be a hand-operated surgical instrument or an instrument in a telerobotic surgical system. The present disclosure contemplates that such a surgical instrument is operatively connected to a computer control system that independently controls each of the gripping, cutting, and fusing procedures of the instrument based on separate inputs. To initiate a desired function, the operator must select the appropriate input control function.

The present disclosure further contemplates that a single component of the working end of the instrument may be used to control both the gripping and cutting procedures through, for example, control of first and second ranges of motion of the component. Control of the energy application for the fusing procedure may be through individually received inputs or via the system computer in response to a system input. The present disclosure further contemplates that two procedures, although independently controlled, may be initiated at the same time in an automated manner. For example, the cutting and energy application functions may be simultaneously started after tissue is grasped to permit substantially simultaneous fusing and cutting of the tissue in an automatic process.

FIGS. 1A to 1E are diagrammatic plan views of a working end of a surgical instrument including a jaw closure and tissue cutting mechanism. Details of such a mechanism are described in, for example, U.S. Pat. No. 6,905,497 B2, entitled "Jaw Structure for Electrosurgical Instrument" (filed May 31, 2003) and U.S. Patent Application Pub. No. 2003/0114851 A1, entitled "Electrosurgical Jaws for Controlled Application of Clamping Pressure" (filed Dec. 13, 2001), both of which are incorporated herein by reference in their entirety. The following description highlights features associated with the present teachings. It should be understood that aspects of the present disclosure may be implemented with the various details shown in these two references (e.g., two movable jaws, one fixed and one movable jaw, jaws allowed to move apart slightly near the jaw fulcrum, etc.). It should be further understood that although the description below is in the context of an electrosurgical tool that fuses and cuts tissue, the same aspects may be applied to other instruments that may use a similar jaw closure and cutting architecture, such as surgical staplers.

Figure 1A:
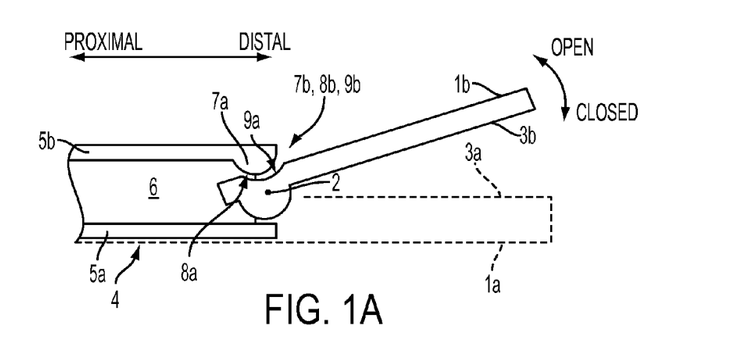
FIGS. 1A to 1E are diagrammatic plan views of a jaw closure and tissue cutting mechanism in accordance with the present teachings.

FIG. 1A shows a set of jaws 1a and 1b. Jaw 1a (shown in phantom line to more clearly illustrate operating features) is fixed in position with reference to the distal end of a surgical instrument shaft (not shown), and jaw 1b pivots with reference to jaw 1a at fulcrum 2 so that the inner faces 3a, 3b of the jaws face each other when the jaws are closed. Electrodes (FIG. 2) configured to receive electrosurgical energy for tissue fusing are positioned on the jaws and in one implementation form a part of the inner faces 3a, 3b.

Figure 1B:
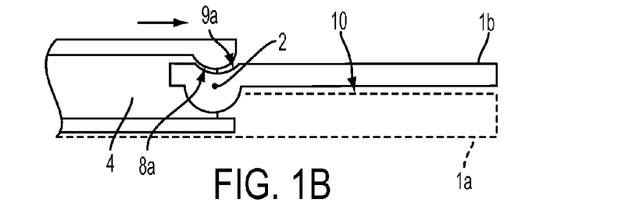
Figure 1C:
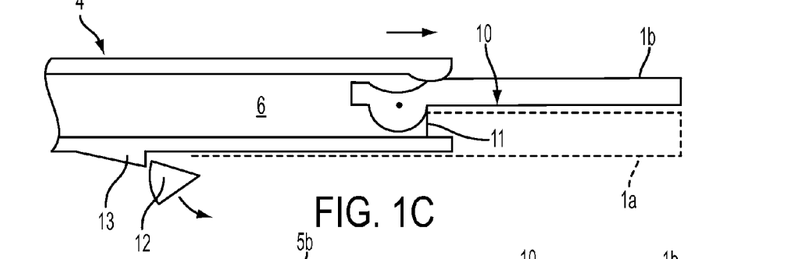
Figure 1D:
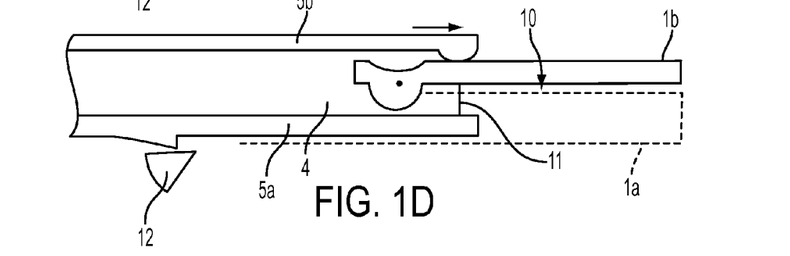
Figure 1E:
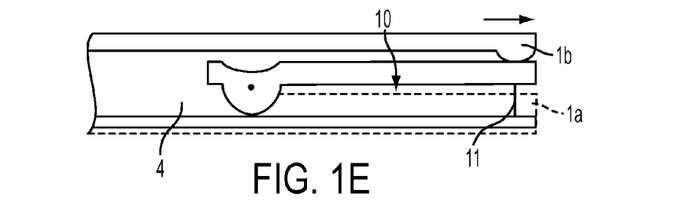

A reciprocating element 4 is movable relative to jaws 1a, 1b, between a full proximal position (see FIG. 1A) and a full distal position (see FIG. 1E). The reciprocating element 4 performs two functions. First, the reciprocating element 4 closes the jaws together. In the depicted implementation, reciprocating element 4's cross section is I-shaped, so that at least the distal part of reciprocating element 4 is shaped as an I-beam. As such, reciprocating element 4 includes a lower jaw closure flange 5a, an upper jaw closure flange 5b, and a connecting web 6 that connects the two flanges 5a, 5b. At the distal end of reciprocating member 4, upper jaw closure flange 5b is extended to include two shoulder elements 7a and 7b (hidden behind 7a). These shoulder elements 7a, 7b include cam surfaces 8a, 8b that engage with corresponding cam surfaces 9a, 9b on jaw 1b.

It can be seen from FIG. 1A that as reciprocating element 4 moves in a proximal direction to a full proximal position, as indicated by the arrow, cam surfaces 8a, 8b engage with corresponding cam surfaces 9a, 9b, which causes jaw 1b to pivot around fulcrum 2 towards an open position as shown. Similarly, as shown in FIG. 1B, as reciprocating element 4 moves in a distal direction towards the end tip of the instrument, as shown by the arrow, cam surfaces 8a, 8b engage with corresponding cam surfaces 9a, 9b to pivot jaw 1b around fulcrum 2 towards a closed position. In the closed position, a small gap 10 exists between jaw 1a and jaw 1b. Tissue to be fused and cut is held in gap 10 between the two jaws 1a, 1b.

FIG. 1C shows that as reciprocating element 4 moves distally from the position shown in FIG. 1B, a clamping force begins to be applied to tissue between the jaws 1a, 1b. The clamping force is initially from the jaws being compressed between shoulder elements 7a, 7b and lower jaw closure flange 5a. At the near-proximal position illustrated in FIG. 1C, this clamping force is small. The clamping force becomes uniformly applied along the length of the jaws as the jaw closure flanges 5a, 5b move along the jaws, as shown in FIGS. 1D and 1E.

FIG. 1C also illustrates reciprocating element 4's second function, which is to cut tissue clamped between the jaws 1a, 1b. As shown, the distal edge 11 of web 6 is a tissue cutting blade. Alternatively, edge 11 represents an electrosurgical energy cutting element as described in more detail in the references above. It can be seen that as reciprocating element 4 moves distally, blade 11 enters gap 10 and will cut any tissue securely held between jaws 1a, 1b. To prevent inadvertent cutting, therefore, a mechanical stop 12 engages part 13 of reciprocating element 4 to limit reciprocating element 4's distal travel and resultant tissue cutting. Alternatively, a similar mechanical stop may engage another component that causes reciprocating element 4 to move.

FIG. 1D shows that if stop 12 is moved away from engaging reciprocating element 4, then reciprocating element 4 may continue to move distally. Blade 11 enters gap 10 and cuts tissue grasped between jaws 1a, 1b. At the same time, upper and lower jaw closure flanges 5a, 5b begin to apply a high clamping force against the jaws and consequently against the tissue held between the jaws in gap 10.

FIG. 1E shows reciprocating element 4 at a full distal position, at which a high and uniform clamping force is applied to jaws 1a and 1b. At the position shown in FIG. 1E, blade 11 has cut any tissue in gap 10, and the necessary high clamping force has been applied to the tissue in gap 10 to enable an application of electrosurgical energy for successful tissue fusing.

It can be seen that reciprocating element 4 is representative of similar implementations in other devices. For example, it is known that linear surgical staplers use a sled that translates along a staple cartridge to force staples through tissue for formation against an anvil, which is typically a jaw similar in concept to jaw 1b. A tissue cutter, such as a knife blade, is fixed to the sled and cuts tissue clamped between the staple cartridge and anvil in a manner similar in concept to blade 11. If a portion of the reciprocating element is configured to bend (e.g., in a single degree of freedom orthogonal to the plane of jaw closure), then the surgical tool can be implemented with a distal end wrist capability to facilitate maneuverability inside the body, such as during minimally invasive surgery (e.g., laparoscopic or thoracoscopic surgery). Wrist aspects are discussed in more detail below. Alternatively, a portion of the reciprocating element may be allowed to flex with a more gradual bend, so that the shaft between an actuator and the surgical end effector may be made flexible.

Figure 1F:
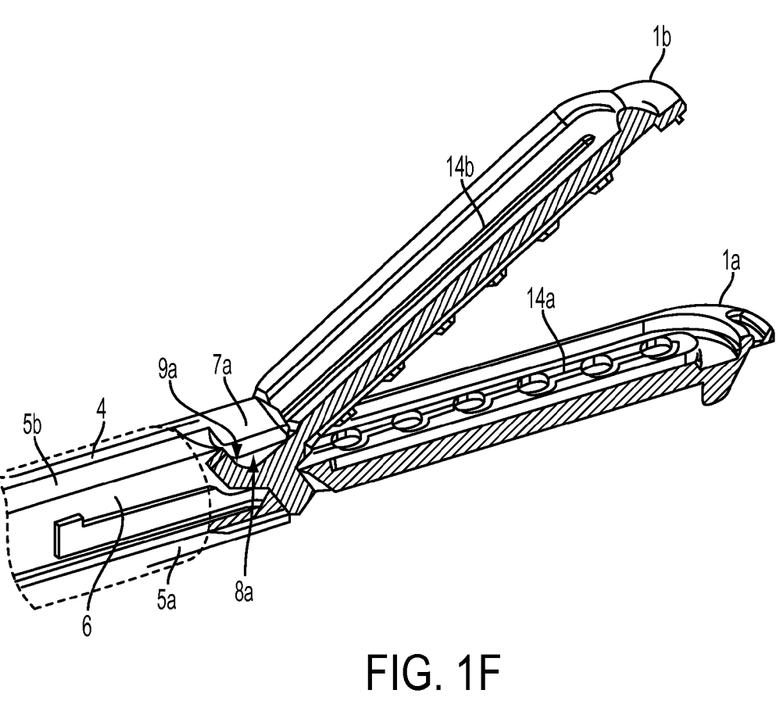
FIG. 1F is a perspective cutaway view of an embodiment of the mechanism illustrated in FIGS. 1A to 1E in accordance with the present teachings.

FIG. 1F is a perspective cutaway view of an embodiment of the surgical instrument working end mechanism illustrated in FIGS. 1A to 1E. FIG. 1F shows an exemplary embodiment in which cam surfaces 8a and 9a interact to open and close the jaws 1a, 1b. FIG. 1F also shows how lower and upper jaw closure rails 5a, 5b slide along the jaws 1a, 1b to clamp the jaws together. Finally, FIG. 1F shows that web 6 slides through slot 14a in jaw 1a and slot 14b in jaw 1b as reciprocating element 4 moves distally. Thus tissue cut by blade 11 (hidden from view) at the distal end of web 6 remains clamped between the two jaws 1a, 1b.

Figure 2:
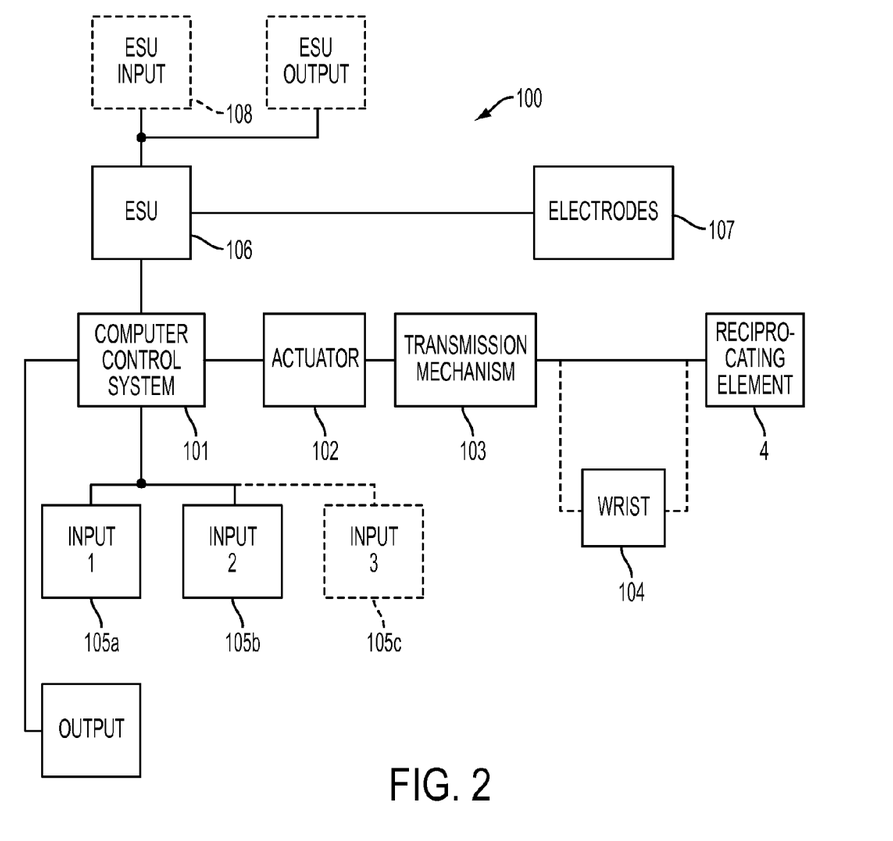
FIG. 2 is a diagrammatic view of a computer-controlled surgical system in accordance with the present teachings.

FIG. 2 is a diagrammatic view of an exemplary embodiment of a computer-controlled surgical system 100 in accordance with an aspect of the present disclosure. In one implementation, surgical system 100 is a general purpose telerobotic surgical system, such as the da Vinci® Si™ Surgical System commercialized by Intuitive Surgical, Inc., Sunnyvale, Calif. In another implementation, surgical system 100 is a hand-held tool similar to current hand-held electrosurgical or stapling tools, such as the powered iDrive™ stapler commercialized by Covidien AG and the hand-actuated EnSeal® tissue sealing devices commercialized by Ethicon Endo-Surgery, Inc. Persons familiar with robotic and medical device engineering will understand many of the routine mechanical and medical device implementation details, which are omitted from this description to avoid prolix explanation.

Surgical system 100 includes a computer control system 101 that controls system 100 operations in whole or in part. Computer control means control by any device that performs computations to effect such control, and it includes, by way of non-limiting example, control using a microprocessor, a microcontroller, a digital signal processor, a field programmable gate array, a programmable logic device, an optical computer, or any other form of programmable control that performs computations. Shared control occurs when part of the control is done by computer control, and part of the control is done by other means, such as manual operation. Control system 101 is configured to carry out one or more of the various implementations described herein.

Actuator 102 (e.g., a telerobotic slave servo actuator, an electric motor in a hand held tool, and the like) is coupled to and controlled by control system 101. In turn, reciprocating element 4 is coupled to actuator 102 via transmission mechanism 103, so that actuator moves reciprocating element 4 proximally and distally as described herein. Transmission mechanism 103 may include various mechanical devices such as levers, cams, gears, or lead screws in order to transmit actuation force and/or torque from actuator 102 to reciprocating element 4. An example of shared control is if movement of reciprocating element 4 is controlled over one range of travel as a result of computer control, and controlled over a second range of travel as a result of manual control (the actuator 102 being, in effect, two separate actuating components, the one back driving the other and any of the other's relevant associated transmission mechanism components).

In one optional implementation, reciprocating element 4 is coupled to transmission mechanism 103 via a wrist 104. Transmitting force and/or torque through a wrist mechanism or flexible shaft, as described above, is known to persons familiar with robotics and powered medical device design. For example, a bendable band may be pushed and pulled through a single degree of freedom (DOF) wrist, a cable (e.g., a Bowden cable or the like) may be pushed and pulled through a two-DOF wrist, and a flexible torque tube may be used to transmit torque through a one- or two-DOF wrist. Exemplary structures and methods for transmitting force and/or torque through a wrist are described, for example, in U.S. Patent Application Publication No. 2012/0215220, entitled "Fusing and Cutting Surgical Instrument and Related Methods" (filed Feb. 17, 2012); U.S. Pat. No. 7,303,107 B2, entitled "Surgical Stapling Apparatus" (filed Jul. 19, 2006); U.S. Pat. No. 7,784,662 B2, entitled "Surgical Instrument with articulating shaft with a single pivot closure and double pivot frame ground" (filed Apr. 7, 2005); and U.S. Pat. No. 7,861,906 B2, entitled "Surgical stapling apparatus with articulatable components" (filed Feb. 14, 2008), all of which are incorporated herein by reference in their entireties.

As shown in FIG. 2, computer control system 101 receives at least two inputs 105a, 105b that result in motion of reciprocating element 4. For example, in one exemplary implementation a first input 105a, is a pincer type grip master control that when activated moves reciprocating element 4 slave to open and close jaws 1a and 1b as described above with reference to FIGS. 1A to 1C. Computer control system 101 prevents any input from first input 105a from commanding actuator 102 to move reciprocating element 4 to a position distal from the position shown in FIG. 1C, so that operator control via first input 105a will not result in inadvertent cutting of tissue between jaws 1a, 1b. This feature is a key safety aspect, since with purely mechanical implementations if the reciprocating element mechanical limit stop 12 is mistakenly out of position, tissue may be cut when only grasping between jaws 1a,1b is intended.

Therefore, in accordance with an aspect of the present disclosure, the user activates second input 105b in order to move reciprocating element 4 into gap 10 and cut tissue, as illustrated in FIGS. 1D and 1E. Second input 105b is, for example, a foot pedal. In some implementations, an optional third input 105c is included in system 100. Details concerning various input device configurations (e.g., inputs 105) are described below.

FIG. 2 also shows an Electrosurgical Unit (ESU) 106 coupled to electrodes 107 on jaws 1a, 1b. In some implementations, as shown, ESU 106 is coupled to computer control system 101 so that ESU 106 receives commands via inputs 105a, 105b, and optionally 105c, to introduce electrosurgical energy to electrodes 107. In other implementations, ESU 106 and electrodes 107 are separate from system 100, and inputs received for computer control system 101 have no control over ESU 106. In such implementations, one or more separate ESU inputs 108 (e.g., foot pedal control) are used to operate ESU 106. Thus, ESU 106 can be controlled either from its individual control input or via the system computer (computer control system 101) in response to a system input.

Figure 3:
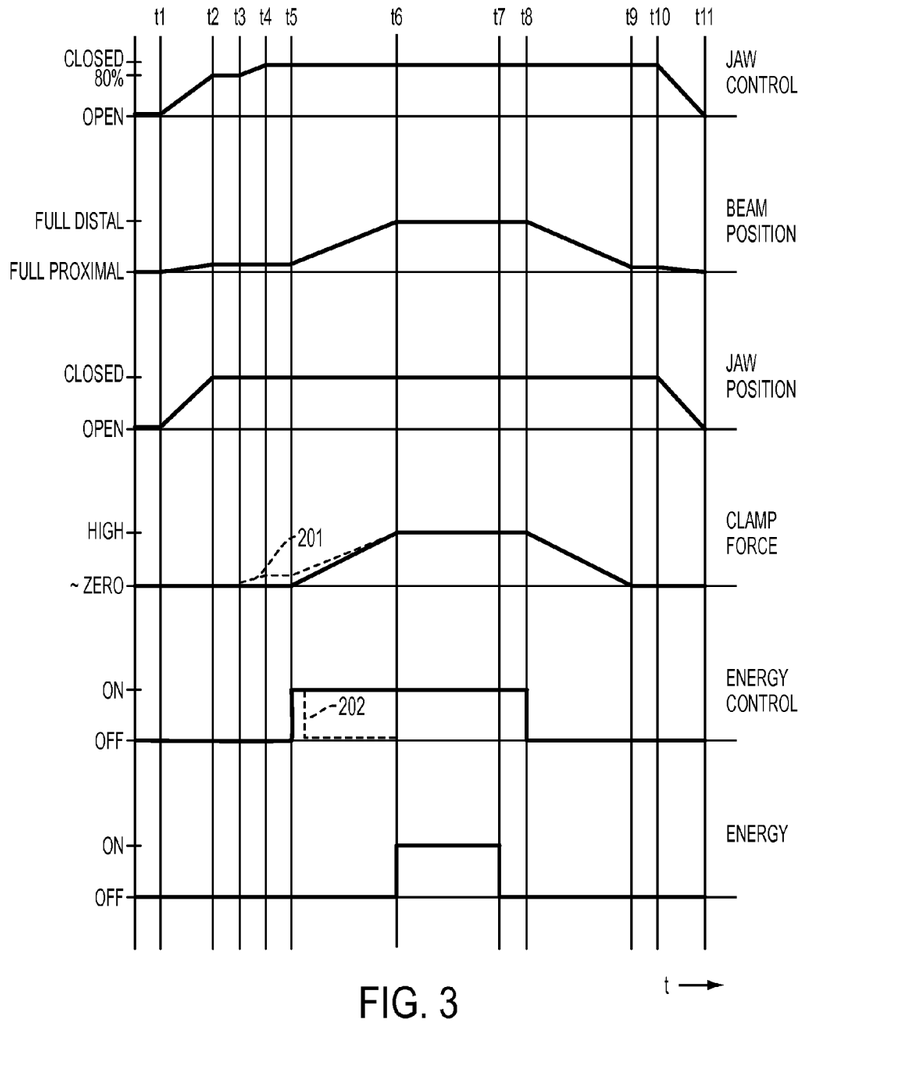
FIG. 3 is a diagram that illustrates an implementation of a process in accordance with the present teachings.

FIG. 3 is a diagram that illustrates an implementation of a process in accordance with an aspect of the present disclosure. Six conditions are shown from top to bottom: jaw position control, reciprocating element (beam) position, jaw position, jaw clamp force, energy application control, and energy application. This process, and the ones illustrated in FIGS. 4 and 5, along with the variations described herein, can be implemented in various systems ranging, for example, from large, general purpose, computer-controlled teleoperated surgical robots to hand-held, single purpose, computer-controlled surgical tools. As this process is described, various alternative implementations are also described.

At t1 an operator begins to operate a jaw position control (e.g., first input 105a). This control is typically operated by one or more digits of the hand as an emulation of control of a purely hand-operated instrument, such as a small forceps. For example, in one surgical robotic system, the jaw position is controlled by the operator squeezing pincer elements together with two digits. Alternatively, a digit-operated trigger, a foot pedal, or other control input may be used. Similar control may be implemented in a hand-held tool, which may use a trigger or hand grip function to control the jaw position.

As the operator begins to move the jaw position control towards the jaw closed position, the reciprocating element 4 moves slightly in the distal direction. As described above, this distal direction movement moves the jaws from the open position to the closed position. As shown in FIG. 3, at t2 the jaw position control has been moved to command the jaws to fully close, the reciprocating element has moved slightly in the distal direction, and the jaws move to a fully closed position in which tissue to be sealed and cut is held between the jaws.

As also shown, at t2 the clamping force on tissue held between the jaws is shown to be substantially zero (~zero). In fact, the tissue is held between the jaws at a light pinching force sufficient to keep the tissue from sliding between the jaws. For purposes of this description, the clamping force is considered to be ~zero. It will be understood, however, that even at this light holding force, electrosurgical energy may be applied to begin to fuse the tissue.

Further shown at t2, the jaw position control is not fully closed. Instead, full jaw closure is commanded when the jaw control is closed to an intermediate position, such as about eighty percent (80%) closed. In certain implementations, reserving a small amount of jaw position control motion is a key feature that provides the operator with a small amount of haptic feel, allows the operator to control a small amount of additional clamping force, or provides a safety margin that must be crossed to continue with the process. In optional implementations, however, jaw position control and jaw position are correlated so that one hundred percent (100%) jaw position control closure is required to fully close the jaws. Details on reservation of jaw control are described, for example, in U.S. patent application Ser. No. 13/655,999, entitled "Grip Force Control for Robotic Surgical Instrument End Effector" (filed Oct. 19, 2012), which is incorporated herein by reference in its entirety.

In accordance with an aspect of the present disclosure, the operator is free to control jaw position within the range illustrated by the conditions at t1 and t2 without concern that the reciprocating element will cut tissue that is between the jaws. The reciprocating element will move distally a sufficient amount to begin to cut tissue between the jaws only when at least a second condition occurs, so that a combination of at least two conditions is required before tissue cutting occurs, and the second condition is more than a mere safety release condition.

At t3 the operator begins to close the jaw position control the remaining twenty percent (20%), so that at t4 the jaw position control is fully closed. In some implementations, this further jaw position control closure has no effect on the reciprocating element position, jaw position, or clamping force. In alternative implementations, however, this small control motion moves the reciprocating element slightly more distally, which in turn begins to apply a light clamping pressure to tissue between the jaws. This situation is illustrated in dashed line at 201. In implementations in which jaw position control and jaw position are correlated, the full jaw position control closure may command either a substantially zero clamping force or a small amount of clamping force. In accordance with an aspect of the present teachings, therefore, the operator is still free to control jaw position within the range of being fully open to applying a small clamping force without concern that the reciprocating element will cut tissue that is between the jaws.

In some optional implementations, the fully closed (or reaching another closure threshold, such as ninety-five percent) jaw position control condition is required as a safety threshold before the computer control system 101 will allow the reciprocating element 4 to move a sufficient distance to begin to cut tissue between the jaws.

In various optional implementations, if at any time prior to t5 the jaw position control is moved to open the jaws, the jaws will open.

At t5, with the tissue to be sealed and cut between the jaws, the operator gives the command to apply energy (e.g., second input 105b or a separate input directly associated with ESU 106), which is effectively a command to seal and cut the clamped tissue. An example of such a command is the operator pressing or otherwise actuating an input device such as a foot pedal or button (e.g., one color-coded yellow in accordance with industry standards). As shown in FIG. 3, when the energy control command is received, the reciprocating element is moved to its full distal position so that a high force clamp is applied to tissue between the jaws. By the nature of the design, it can be seen that as the high force clamp is applied, tissue between the jaws is cut. At t6 the reciprocating element is at its full distal position, high force clamp is applied to the tissue, and the tissue has been cut by the reciprocating element.

In the depicted implementation, at t6 electrosurgical energy is automatically applied to electrodes in the jaws to fuse the tissue clamped between the jaws. The electrosurgical energy is applied until tissue fusion is sensed (as is known in the art) at t7, at which time the energy is removed. Consequently, at t7 the clamped tissue has been cut, and the tissue on either side of the cut has been fused.

As shown in FIG. 3, the reciprocating element remains at its distal-most position (the full distal position) until the energy control input is returned to the off position. When at t8 the energy control input is moved to the off position, the reciprocating element is automatically moved distally so that at t9 the reciprocating element is at a near full proximal position, the clamp force returns to substantially zero, and the jaws remain closed. Then, to open the jaws, at t10 the operator opens the jaw position control, the reciprocating element moves to its full proximal position, and the jaws fully open, as shown at t11. At this position, in one implementation the system 100 is then ready to perform one or more subsequent tissue fusing and sealing operations, or tissue grasping operations, as described herein.

In addition to the illustrative implementation and the variations described above, many additional variations may be applied in other implementations. The options described above and below may be combined in any way practical, as long as one or more particular option does not prevent the implementation of an embodiment with one or more other options. These various options apply to both relatively larger teleoperated surgical robots designed to operate a variety of surgical tools and to relatively smaller hand-held surgical tools designed to operate as a dedicated single instrument type.

As described above, the cutting and fusing actions are combined with the actuation of a single input, such as a foot pedal or button. Alternatively, however, the cutting and fusing actions may be separately controlled. Such separate control gives the operator the capability to cut clamped tissue without any tissue fusion taking place (a so-called "cold cut"). If tissue fusion is desired, then a second control is operated, such as a second foot pedal or button. For example, to implement cutting, a blue-colored foot pedal or button is pressed (e.g., second input 105b is provided), and to implement tissue fusion, a yellow-colored foot pedal or button is pressed (e.g., third input 105c or an input directly associated with ESU 106 is provided). As an alternative to foot pedals or buttons, various other devices may be used to input the cut and fuse commands, such as a switch positioned near the jaw position control input, a voice command, etc. A key advantage, however, is that the input device used to control the cutting function (e.g., second input 105b) is separate from the device used to control the jaw position and tissue clamping force (e.g., first input 105a). Thus, even though a single reciprocating element is used to both actuate jaw position and carry out tissue cutting, two different input devices are used to control these two functions. These separate inputs prevent an inadvertent over-actuation of the jaw position control input, as may occur when a reciprocating element limit switch has been incorrectly positioned, and unwanted tissue cutting.

In some instances the two (or more) separate inputs are combined in a single type of input device. This single type of input device travels over a first range of motion to command jaw position, and it travels over a second range of motion or moves to a second position outside the first range of motion to control cutting. For example, the reciprocating element's first range of motion, which controls jaw opening and closing, may be controlled by a first range of motion of a spring-loaded pincer mechanism pinched by digits of the hand. The reciprocating element's second range of motion, which is associated with tissue cutting, is then controlled by a second range of motion of the pincer mechanism. This second range of motion is separated from the first range of motion by a clear divider, such as a noticeably higher spring force, a noticeable haptic detent, etc. Elements having two controllable ranges of motion are described, for example, in U.S. patent application Ser. No. 13/655,999, entitled "Grip Force Control for Robotic Surgical Instrument End Effector" (filed Oct. 19, 2012), which is incorporated herein by reference in its entirety. Similarly, a spring-loaded foot pedal may have two clearly divided ranges of motion, or an input may be difficult to move into a second operating position or direction (akin to a reverse gear "lockout" feature in some automobile manual transmissions), or a second mechanical input must be held in order to move the first input into the second range or position (akin to button that must be pressed on an automobile automatic transmission position selection lever). A key feature is still that while the input is operated to control jaw position, inadvertent tissue cutting is prevented, since the input cannot move into the second range of motion or position without a positive action by the operator each time a transition to the second range of motion or position is desired.

Whether a single input is used to control both cutting and fusing, or whether separate inputs are used, the required input may be continuous, such as holding a spring loaded pedal or button in an ON position, or the input may be a brief pulse that starts the function. If the cutting and sealing functions are combined, then a single tap of a foot pedal or button may be used to start the cutting and sealing process between t5 and t7 as shown in dashed line at 202. Likewise, a single tap on one foot pedal may start the cutting function and a single tap on a second pedal may start the fusing function. Control logic prevents the fusing function from beginning if the second pedal is tapped before the reciprocating element is in the correct full distal position. A combination of a tap on one input and a continuous hold on another input may be used. An optional warning (audio, video) may be output that advises the operator that the fusing function has not started. If a tap is used to control the tissue cutting function alone, then the reciprocating element may automatically return to the full- or near-proximal position after the cutting, or a second input, such as a second tap or the opening of the jaw position control, may be used to return the reciprocating element to the full- or near-proximal position.

As a safety feature, moving the jaw position control towards open (e.g., opening the grip control) at any time during the process may stop a portion or all of the process implemented up to that time. For example, if the jaw position control is opened mid-way through the tissue cutting function, the reciprocating element is returned to its full- or near-proximal position and the jaws are moved to an open position. The operator then manages any bleeding or other effect of the cutting. Likewise, if the jaw position control is opened midway through the tissue fusing function, the electrosurgical energy is removed from the electrodes so that the fusing function stops, and the reciprocating element returns to its full- or near-proximal position, either automatically or as the result of another control input.

Similarly, if the combined or individual cutting and fusing functions are controlled by a continuous input, such as a continuous foot pedal or button press, releasing the input may stop the cutting or fusing function and variously keep the reciprocating element in place or automatically returning the reciprocating element to its full- or near-proximal position.

In some implementations, the control system outputs an indication that the cut function and/or the fusing function are complete and indicated successful. In such implementations, if a situation occurs in which the correct conditions to carry out the cutting or the sealing function has occurred, but the expected indication is not output to the operator so that the operator suspects the function was not successful, or if the system outputs a second indication that the expected function was unsuccessful, various approaches may be used. Exemplary user interface systems providing information regarding an actual or expected outcome of a computer-controlled surgical process are described in, for example, U.S. Patent Application Publication No. 2012/0248167, entitled "Methods and Systems for Detecting Staple Cartridge Misfire or Failure" (filed May 15, 2012); U.S. Patent Application Publication No. 2012/0209314, entitled "Methods and Systems for Indicating a Clamping Prediction" (filed Jan. 13, 2102); U.S. Patent Application Publication No. 2012/0205419, entitled "Methods and Systems for Detecting Clamping or Firing Failure" (filed Jan. 13, 2012); and U.S. Patent Application Publication No. 2012/0209288, entitled "Indicator for Knife Location in a Stapling or Vessel Sealing Instrument" (filed Jan. 13, 2012), all of which are incorporated by reference herein in their entireties.

For example, if the operator suspects or receives an indication that the tissue cutting function was unsuccessful, the system may be configured to permit the operator to attempt the cutting function again, or to prevent the operator from attempting the cutting function again, or to limit the number of subsequent attempted cutting functions. To recover from an unsuccessful cutting situation, the system may be variously configured as described above to have the reciprocating element move to the full- or near proximal position so that the jaws can be opened.

Similarly, if the operator suspects or receives an indication that the tissue fusing function was unsuccessful, the system may be configured to permit the operator to attempt the fusing function again, or to prevent the operator from attempting the fusing function again, or to limit the number of subsequent attempted fusing functions. To recover from an unsuccessful fusing situation, the system may be variously configured as described above to have the electrosurgical energy removed from the jaws and the reciprocating element move to the full- or near proximal position so that the jaws can be opened.

If at any time the reciprocating element is commanded to return to a full proximal position so that tissue may be removed from the jaws, but the full proximal position is not sensed, the control system may output a warning to the operator that indicates that the reciprocating element is stuck in an intermediate position. The system may be configured to attempt to recover by automatically moving the reciprocating element distally and then once again to move proximally in an attempt to achieve the full proximal position, or by dithering the reciprocating element while urging it towards the full proximal position, or by allowing the operator to attempt to move the reciprocating element by moving an input device, such as the device used to initiate the cut function.

Figure 4:
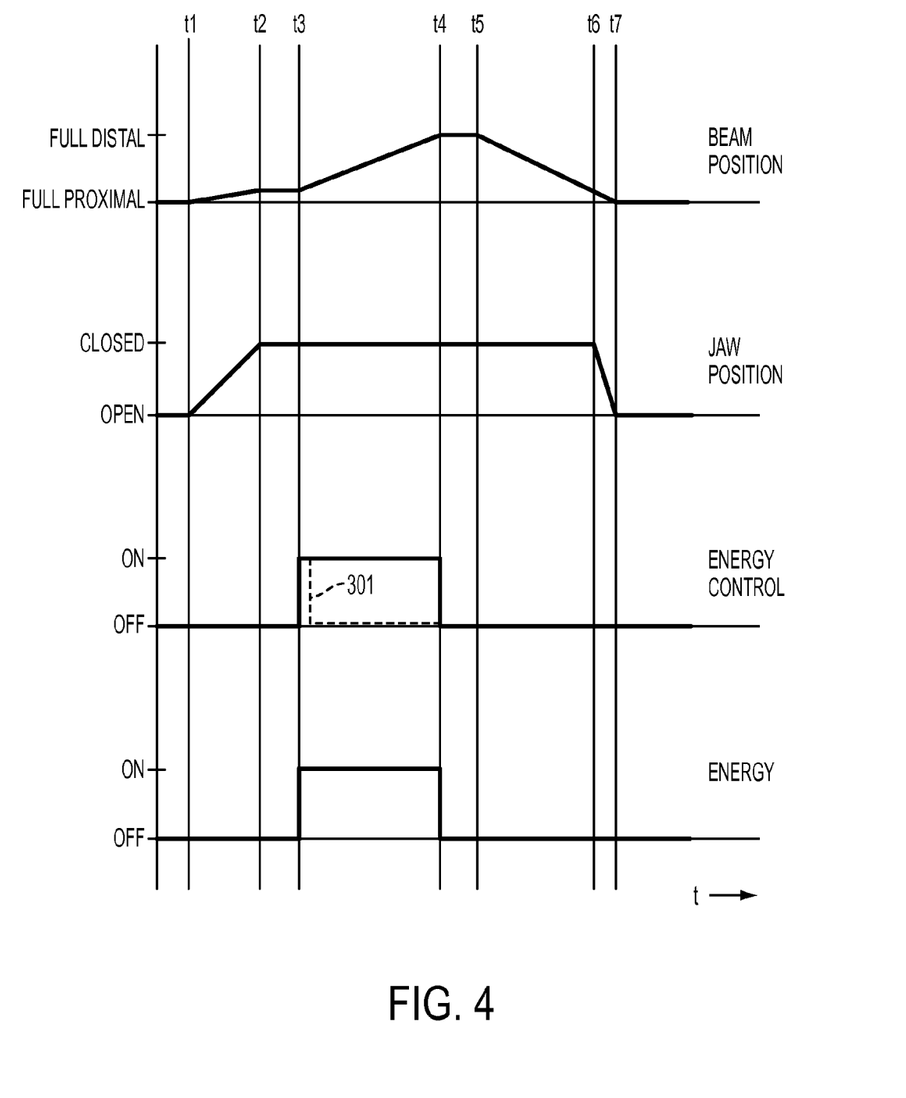
FIG. 4 is a diagram that illustrates an implementation of an alternative process, in accordance with the present teachings.

FIG. 4 is a diagram that illustrates an implementation of another process in accordance with an aspect of the present disclosure. Four conditions are illustrated from top to bottom: reciprocating element (beam) position, jaw position, energy application control, and energy application. Jaw position control and clamp force are as described above and omitted for clarity.

As shown in FIG. 4, between times t1 and t2 the beam position and jaw position are related as described above. At t3, the operator initiates electrosurgical tissue fusing energy application. This initiation is started by operating a second control system input (e.g., input 105b), other than the input normally used to control jaw position during the tissue grasping function. The energy control may be held in an ON position as shown in FIG. 4, or alternatively may be a short pulse or tap on the input, as shown in dotted line 301. For example, the operator may press and hold a foot pedal, or the operator may tap the foot pedal.

In response to the operator initiating energy application, the control system commands the ESU to apply energy to the electrodes and commands the actuator to move the reciprocating element towards the distal-most position. Thus electrosurgical tissue fusing energy is applied as the reciprocating element moves distally over the jaws. In addition, tissue cutting occurs as the tissue is fused, so that bleeding is controlled. At t4, the reciprocating element is at its full distal position, tissue fusing is complete (as indicated by the ESU), and energy is removed from the electrodes.

At t5 the jaws are commanded to open, either by the operator using the jaw position control input, or automatically by the control system. As the reciprocating element returns to its full proximal position and at t6 passes the near-proximal position as described above, the jaws start to open. At t7 the beam has returned to its full proximal position and the jaws are open.

As described herein, in some instances the control system may be configured to allow the operator to interrupt the fusing and cutting action, so that if the foot is lifted from a foot pedal, or if the jaws are commanded to open by using the jaw position control input, energy application is stopped and the reciprocating element is returned to the proximal or near-proximal position.

Figure 5:
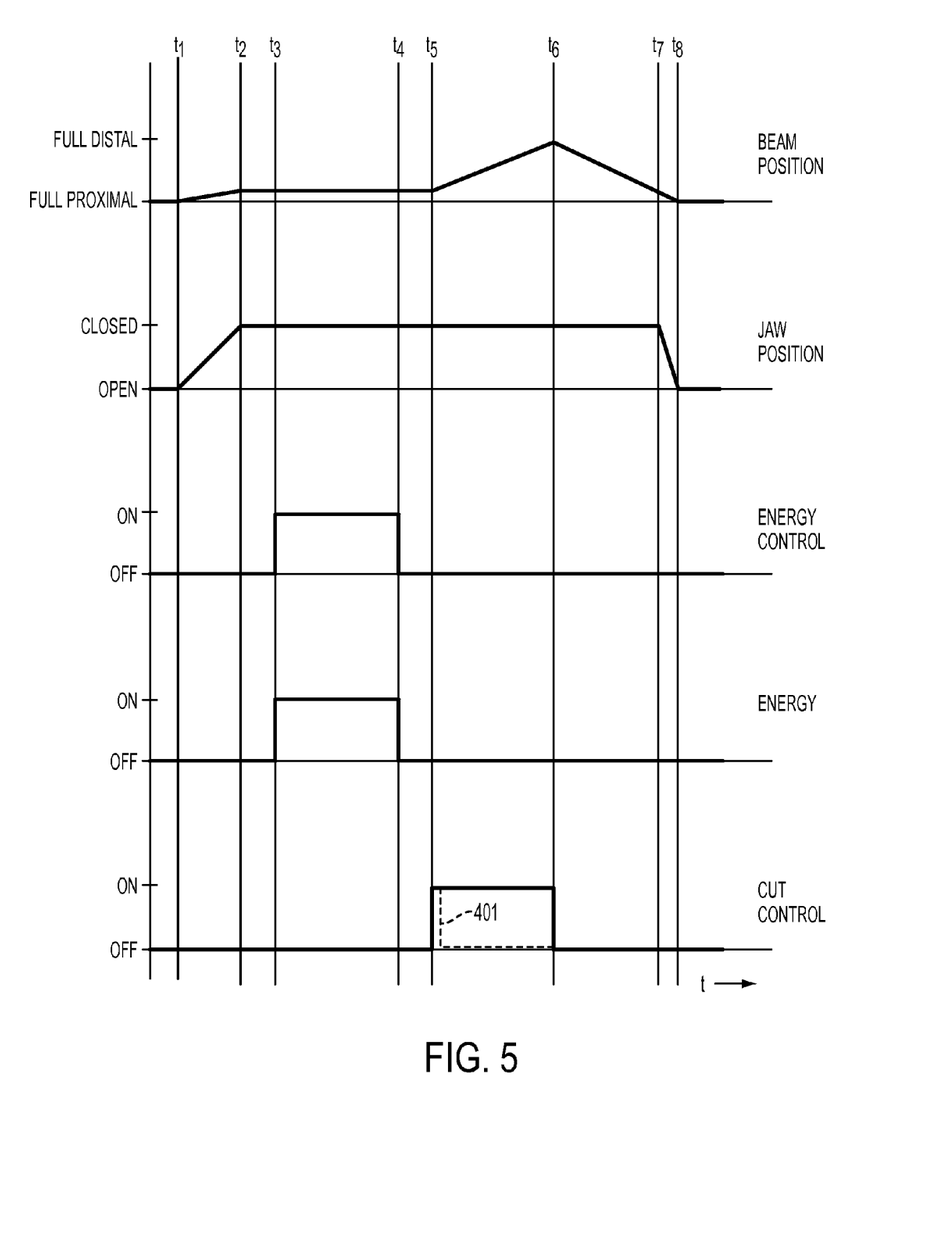
FIG. 5 is a diagram that illustrates an implementation of another alternative process, in accordance with the present teachings.

FIG. 5 is a diagram that illustrates an implementation of yet another process in accordance with an aspect of the present disclosure. Five conditions are illustrated from top to bottom: reciprocating element (beam) position, jaw position, energy application control, energy application, and tissue cutting control. Jaw position control is as described above and omitted for clarity. FIG. 5 illustrates an implementation in which tissue fusing and tissue cutting are separately controlled.

As shown in FIG. 5, between t1 and t2 the reciprocating element position and jaw position are related as described above. At t2 and at t3, the tissue is lightly clamped by the reciprocating element being positioned at the near-proximal position. In some instances, this light clamping is sufficient to allow effective tissue fusing, and show tissue fusing energy application is started at t3. The reciprocating element does not move during the energy application. At t4 the tissue fusing is complete and the energy is removed.

At t5 the operator commands the tissue cutting function to begin. The reciprocating element moves to its distal-most position at t6. As shown, in some instances the reciprocating element moves as long as a cut control input command is received. In other instances, a short pulse initiates the tissue cutting function, as shown in dashed line at 401. From t6 to t8 the reciprocating element returns to its proximal position, either automatically from a control system command or by the operator commanding the jaws to open.

It can be seen that since the tissue fusing and cutting functions are separately controlled, tissue cutting alone can be performed (the cold cutting referred to above).

Further, as described above, the separately controlled tissue fusing and cutting functions may be operated by two separate input devices, or they may be operated by two unique and distinct control functions on the same input device. For example, if a single foot pedal is used to control both tissue fusing and cutting, a single tap or a continuous hold-down may be used to control energy application, and a double tap may be used to command tissue cutting (or vice-versa). It can be appreciated, therefore, that many combinations of one or more input devices (hand operated, foot operated, head operated, elbow or knee or other body part operated, voice operated, eye gaze operated, operated by a second person, etc.) the or each input device providing one or more distinct ranges of motions or positions, can be used to safely and separately control the grasping function versus the fusing function, the cutting function, or the combined fusing and cutting function.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings. For example, various aspects have been described in the context of an instrument used in a surgical robotic system. But these aspects may be incorporated into hand-held instruments as well, with powered or hand-actuated actuation of the various inputs.

Other embodiments in accordance with the present disclosure will be apparent to those skilled in the art from consideration of the specification and practice of the teachings disclosed herein. It is intended that the specification and examples be considered as exemplary only, with a true scope and spirit being indicated by the following claims.

What is claimed is:

1. A computer-controlled surgical system, comprising:
   a surgical instrument having a working end, the working end having a movable mechanical component, movement of the mechanical component performing a clamping function and a cutting function by the working end; and
   a computer control system operably coupled to the surgical instrument and to first and second input devices,
   wherein, in response to a first command received from the first input device, the computer control system controls movement of the mechanical component to perform the clamping function, and
   wherein, in response to a second command received from the second input device, the computer control system controls movement of the mechanical component to perform the cutting function.

2. The computer-controlled surgical system of claim 1, wherein the working end comprises jaws movable between open and closed positions in response to the movement of the mechanical component.

3. The computer-controlled surgical system of claim 2, wherein the mechanical component is a reciprocating element comprising a tissue cutting element, and wherein in response to the first command received from the first input device, the computer control system controls movement of the reciprocating element within a first range to move the jaws from an open position to a closed position without advancing the tissue cutting element into a tissue clamping area of the jaws.

4. The computer-controlled surgical system of claim 3, wherein, in response to the second command received from the second input device, the computer control system controls movement of the reciprocating element within a second range in which the tissue cutting element is advanced into the tissue clamping area to cut tissue between the jaws.

5. The computer-controlled surgical system of claim 2, wherein the mechanical component is configured to engage at least one of the jaws to move the jaws from the open position to the closed position.

6. The computer-controlled surgical system of claim 1, wherein the working end is further configured to perform a fusing function, and
   wherein the computer control system controls the fusing function in response to a third command received from the second input device.

7. The computer-controlled surgical system of claim 6, wherein the second input device comprises a first function control for cutting and a second function control for fusing.

8. The computer-controlled surgical system of claim 1, wherein the computer control system is configured to simultaneously or substantially simultaneously initiate the cutting function and the fusing function of the working end of the instrument in response to input from the second input device.

9. The computer-controlled surgical system of claim 1,
   wherein the working end is further configured to perform a fusing function, and
   wherein the computer control system is further operably coupled to a third input device,
   wherein, in response to a third command received from the third input device, the computer control system controls an energy application to the working end of the surgical instrument to perform the fusing function.

10. The computer-controlled surgical system of claim 9, wherein the computer control system is configured to control the application of energy to the working end of the instrument to perform the fusing function independently of the clamping function and independently of the cutting function of the working end.

11. The computer-controlled surgical system of claim 1,
    wherein the surgical instrument is an electrosurgical instrument, and
    wherein the system further comprises an electrosurgical flux supply unit operably coupled to supply energy to one or more electrodes in the working end of the instrument.

12. The computer-controlled surgical system of claim 1, wherein the first input device is chosen from a trigger mechanism and a gripping mechanism, and wherein the second input device is chosen from a button and a foot pedal.

13. The computer-controlled surgical system of claim 1,
    wherein, in response to the first command received from the first input device, the computer control system controls movement of the mechanical component from a first position at a proximal end portion of the working end to a second position along the working end; and
    wherein, in response to the second command received from the second input device, the computer control system controls movement of the mechanical component of the working end from the second position to a third position at a distal end portion of the working end, the second position being located between the first position and the third position.

14. The computer-controlled surgical system of claim 1, further comprising a mechanical stop, the mechanical stop being actuatable between a first state and a second state, in the first state, the mechanical stop is positioned to engage the mechanical component and to limit the movement of the mechanical component during the clamping function, and in the second state, the mechanical stop is positioned not to engage the mechanical component and not to does not limit the movement of the mechanical component during the cutting function.

15. A method of controlling multiple functions of a working end of a computer-controlled surgical instrument, the working end comprising jaws, the method comprising:

in response to a first command received at a computer control system from a first input device, controlling movement of a movable mechanical component of the working end within a first range to perform a clamping function of the working end of the instrument; and in response to a second command received at the computer control system from a second input device, controlling movement of the mechanical component of the working end within a second range to perform a cutting function of the working end of the instrument.

16. The method of claim 15, wherein controlling the movement of the mechanical component to perform the cutting function includes preventing initiation of the cutting function until the clamping function is completed or substantially completed.

17. The method of claim 15, wherein controlling the movement of the mechanical component over the first range to perform the clamping function comprises controlling the movement of the mechanical component within the first range to move the jaws between an open position and a closed position without cutting tissue clamped between the jaws.

18. The method of claim 15, wherein the mechanical component is a reciprocating element comprising a cutting element, and wherein controlling movement of the mechanical component over the second range to perform the cutting function comprises controlling movement of the mechanical component within the second range to advance the cutting element of the mechanical component and cut tissue clamped between the jaws.

19. The method of claim 18, further comprising controlling an energy application function of the working end of the instrument to perform a tissue fusing function.

20. The method of claim 19, wherein controlling an energy application function includes controlling the application of energy to the tissue clamped between the jaws in response to the second command received from the second input device.

21. The method of claim 19, wherein controlling the application of energy to the tissue clamped between the jaws includes simultaneously or substantially simultaneously initiating cutting and fusing of the tissue clamped between the jaws in response to the second command received from the second input device.

22. The method of claim 19, wherein controlling the application of energy to the tissue clamped between the jaws includes controlling the application of energy to perform the fusing function independently of the cutting function and independently of the clamping function.

23. The method of claim 22, wherein controlling the application of energy includes controlling the application of energy in response to a third command received from a third input device.

24. The method of claim 15, wherein:

wherein controlling movement of the mechanical component of the working end within the first range comprises controlling the movement of the mechanical component from a first position at a proximal end portion of the working end to a second position along the working end; and wherein controlling movement of the mechanical component of the working end within the second range comprises controlling the movement of the mechanical component from the second position to a third position at a distal end portion of the working end, the second position being located between the first position and the third position.

* * * * *